United States Patent [19]

Ercoli

[11] 4,344,956

[45] Aug. 17, 1982

[54] OXOTETRAHYDROTHIOPHENES

[76] Inventor: Nicolò Ercoli, Residencia La Hacienda (23 L) Avenida Principal Las Mercedes, Caracas, Venezuela

[21] Appl. No.: 674,068

[22] Filed: Apr. 6, 1976

[51] Int. Cl.$^3$ ............... A61K 31/42; A61K 31/54; C07D 333/16; C09B 23/16

[52] U.S. Cl. ............................ 424/272; 424/426; 424/248.4; 424/249; 424/250; 424/256; 424/269; 424/274; 424/275; 549/63; 549/60; 549/59; 542/420; 542/406

[58] Field of Search ............... 424/272, 246, 248.4, 424/249, 250, 256, 269, 274, 275; 549/63, 60, 59; 542/406, 420

[56] References Cited

U.S. PATENT DOCUMENTS 3,546,216 12/1970 Dunn ........................... 260/332.1

Primary Examiner—Alan Siegel

Attorney, Agent, or Firm—Berman, Aisenberg & Platt

[57] ABSTRACT

Biological activity is retained while reducing toxicity to animals, particularly mammals, e.g. humans, when a physiologically-active and pharmacologically-acceptable compound (having or structurally modified to have an aldehyde function) is condensed with any of the six (mono)amino(mono)oxotetrahydrothiophenes, e.g. homocysteine thiolactone, to form a Schiff Base (a 4-butyrothiolactone-2-imine or γ-thiobutyrolactone-α-imine). The invention is directed to every Schiff Base which is a condensate of a physiologically-active and pharmacologically-acceptable compound with a (mono)amino(mono)oxotetrahydrothiophene. These Schiff Bases have a unifying common property in reduced toxicity, while maintaining the biological properties "carried" by the imine substituents. They concurrently have at most an insignificant adverse affect on pharmacological activity.

25 Claims, No Drawings

OXOTETRAHYDROTHIOPHENES

SUMMARY

The toxicity of physiologically-active and pharmaceutically-acceptable compounds is often a factor which is limiting (at least to some extent) of the use of such compounds. Whenever any of these active compounds has an aldehyde function in its molecular structure or has a molecular structure to which an aldehyde function can be bound and the original or implanted aldehyde function is one which is capable of forming a Schiff Base with a primary amine, the toxicity thereof is reduced by condensing it with a (mono)amino(-mono)oxotetrahydrothiophene (free from further oxygen or other substituents on the tetrahydrothiophene ring) to form the corresponding butyrothiolactoneimine. The present invention is thus directed to a manner and a means for reducing the toxicity of physiologically-active compounds; the manner involves condensing an active compound (with a suitable aldehyde function or modified to contain a suitable aldehyde function) with any of six (mono)amino(mono)oxotetrahydrothiophenes according to recognized and established procedures, and the means is the resulting condensate, which is a butyrothiolactoneimine. In the broader sense the invention encompasses every physiologically-active and pharmaceutically-acceptable butyrothiolactoneimine wherein the thiolactone ring is otherwise free from oxygen or further substituents and wherein the imine nitrogen is directly bound to the thiolactone ring.

While the actual biological activity of the condensate may vary in intensity somewhat depending upon the particular tetrahydrothiophene with which the physiologically-active compound is condensed and may vary somewhat in selectivity depending upon the position in the structure of the physiologically-active compound at which the aldehyde function is bound, the reduction in toxicity is preserved regardless of the tetrahydrothiophene, i.e. within the limited scope instantly contemplated. By "selectivity" is understood that particular pharmacological activities may be emphasized or suppressed to some extent by having the reactive aldehyde function, e.g., aliphatically- rather then aromatically-bound or even by having it bound at different positions on the same ring.

When a selected physiologically-active compound does not have an aldehyde function which is subject to the Schiff Reaction and such function is introduced into the molecular structure of such compound for the purpose of preparing a Schiff Base, the particular activity of the compound which is predominant in the Schiff Base may thus depend upon the actual position in the structure in which the aldehyde function is introduced. In aromatic compounds, e.g., a shift in activity may well be noted, depending upon whether the aldehyde function is placed directly on a ring or on a side-chain. An example of such a shift is observed for such compounds as the phenothiazines.

The impact of this invention is even greater than is immediately apparent from the preceding description because physiologically-active compounds which were not previously regarded as pharmacologically acceptable are now rendered pharmacologically acceptable by the reduction in toxicity imparted thereto by condensation with one of the enumerated tetrahydrothiophenes. The invention, in its broadest aspect, thus extends to and includes all physiologically-active and pharmacologically-acceptable Schiff Bases which are (mono)amino(mono)oxotetrahydrothiophene/aldehyde condensates.

Introducing an aldehyde function [—CHO] on an aromatic, aliphatic or cycloaliphatic carbon is within the skill of the art according to established procedures and does not constitute part of the present invention. Whenever an aldehyde function is referred to in connection with this invention, however, it is one which is bound to a carbon atom and is one which is capable of condensation with a primary amine to form an imine in a manner similar to that of the Schiff Reaction.

DETAILS

The compound, R°—CHO, having an aldehyde function and with which the (mono)amino(mono)oxotetrahydrothiophene is condensed to form a Schiff Base according to this invention is limited only to the extent that the resulting Schiff Base is physiologically active and pharmacologically acceptable and that said compound is capable of undergoing the Schiff Reaction. R° represents (a) aliphatic, such as alkyl having from 1 to 8 carbon atoms, e.g. n-butyl; (b) cycloaliphatic, such as cycloalkyl having from 4 to 7 ring carbon atoms, e.g. cyclohexyl; (c) polycyclic, such as carbocyclic aromatic, e.g. α- or β-naphthyl and 2- or 4-anthryl, heterocyclic aromatic, e.g. 3-isoquinolyl and 1,8-naphthyridin-2-yl, carbocyclic aliphatic, e.g. perhydro-2-naphtyl and 4-adamantyl, heterocyclic aliphatic, e.g. hexahydro-3a,7a-dimethyl-4,7-epoxyisobenzofuran-1,3-dion-5-yl and decahydro-4a,7,9-trihydroxy-6,8-bis(methylamino)-4-oxo-4H-pyrano[2,3-b][1,4]benzodioxine-2-methylene; (d) monocarbocyclic aromatic, e.g. salicyl; (e) monoheterocyclic aromatic, e.g. 3-pyridyl; and (f) monoheterocyclic aliphatic, e.g. 3-morpholinyl, groups, any combination thereof and their therapeutically-functional substitutions.

By "therapeutically-functional substitutions" is intended the entire scope of substituents on any of the enumerated residues or nuclei which negates neither physiological activity nor pharmacological acceptability of the resulting Schiff Base. In fact the "therapeutically-functional substitutions" can, but need not necessarily, impart one or more dominant physiological activities to the Schiff Base.

In the compound, R°—CHO, the carbaldehyde group [—CHO] is directly bound to a carbon atom of —R°. When R° comprises one or more cyclic structures, the carbaldehyde group is not limited to one which is directly attached to a ring carbon atom; it is equally likely to be directly attached to an aliphatic carbon atom of a ring substituent. When directly bound to a ring carbon atom, the ring is, optionally, carbocyclic or heterocyclic, monocyclic or polycyclic, aromatic or cycloaliphatic (saturated or partially unsaturated).

Contemplated (substituted or unsubstituted) cyclic structures within the meaning of R° include 3-pyrrolecarbaldehydes [2-pyrrolecarbaldehydes do not give the Schiff Reaction], 2- or 3-furancarbaldehydes, 2- or 3-thiophenecarbaldehydes, 2-, 3- or 4-pyridinecarbaldehydes, 3-, 4-, 5- or 6-2H-pyrancarbaldehydes, 2- or 3-4H-pyrancarbaldehydes, 2-, 3-, 4-, 5-, 6-, 7- or 8-quinolinecarbaldehydes, 1-, 3-, 4-, 5-, 6-, 7- or 8-isoquinolinecarbaldehydes, 3- or 4-pyrazolecarbaldehydes, 2-, 4- or 5-pyrimidinecarbaldehydes, pyrazinecarbaldehydes, 3-, 4-, 5- or 6-(1,2-4H-oxazin or thiazin)- carbaldehydes, 3-, 4-, 5- or 6-(1,2-2H-oxazin or thiazin)-carbaldehydes, 3-, 4-, 5- or 6-(1,2-3H-oxazin or thiazin)-carbaldehydes, 3-, 4-, 5- or 6-(1,2-5H-oxazin or thiazin)-carbaldehydes, 3-, 4-, 5- or 6-(1,2-6H-oxazin or thiazin)-carbaldehydes, 2-, 4-, 5- or 6-(1,3-2H-oxazin or thiazin)-carbaldehydes, 2-, 4-, 5- or 6-(1,3-3H-oxazin or thiazin)-carbaldehydes, 2-, 4-, 5- or 6-(1,3-5H-oxazin or thiazin)-carbaldeydes, 2-, 4-, 5- or 6-(1,3-6H-oxazin or thiazin)-carbaldehydes, 2-, 3-, 5- or 6-(1,4-2H-oxazin or thiazin)-carbaldehydes, 2-, 3-, 5- or 6-(1,4-4H-oxazin or thiazin)-carbaldehydes, 2-, 3-, 4-, 5-, 6- or 7-indolecarbaldehydes, 1-, 3-, 4-, 5-, 6- or 7-isoindolecarbaldehydes, 1-, 2-, 3-, 5-, 6-, 7- or 8-indolizinecarbaldehydes, cyclizinecarbaldehydes (with the carbaldehyde on either a ring carbon, the methylenebridge carbon or the methyl carbon), 2-, 3-, 4-, 5-, 6- or 7-indolinecarbaldehydes, 2-, 3-, 4-, 5-, 6- or 7-benzofurancarbaldehydes, 1-, 3-, 4-, 5-, 6- or 7-isobenzofurancarbaldehydes, 1-, 2-, 3- or 4-dibenzofurancarbaldehydes, 2-, 3-, 4-, 5-, 6- or 7-benzo[b]thiophenecarbaldehydes, 1-, 2-, 3-, 4- or 9-acridinecarbaldehydes, 1-, 2-, 3-, 4-, 6-, 7-, 8-, 9- or 10-phenanthridinecarbaldehydes, 3, 4, 5, 6, 7 or 8(2H)-chromencarbaldehydes, 3, 4, 5, 6, 7 or 8(4H)-chromencarbaldehydes, 2-, 6- or 8-purancarbaldehydes, 2-, 4-, 6- or 7-pteridinecarbaldehydes, 1,3,5-triazinecarbaldehydes, 3-, 5- or 6-(1,2,4-triazine)carbaldehydes, 4- or 5-(1,2,3-triazine)carbaldehydes and 1-, 2- or 4-tricyclo[3,3,1,1$^{3,7}$]decanecarbaldehydes.

R° is virtually unlimited (except as hereinbefore indicated) other than the requirement that its free bond is on a carbon atom. It is, e.g., an alkyl chain, as in the condensates (imines) obtained with chloralhydrate (trichloracetaldehyde monohydrate), butylchloralhydrate (2,2,3-trichlorobutane-1,1-diol) and valeraldehyde, which results in compounds with sedative-soporific properties; undecylenic aldehyde (10-undecenal) leads to an antifungal imine.

R° represents an aryl or substituted-aryl group in such condensates as those from salicylaldehyde, anisaldehydes and their analogues, which are anti-inflammatory analgesic agents. The homocysteine thiolactone Schiff Base of 3,5-dibromosalicylaldehyde possesses antimicrobial-antifungal properties, while that of 4-benzamidosalicylaldehyde is antitubercular. Preparations (imines) with local anaesthetic action are obtained with aldehydes of p-amino-alkyl-, e.g. p-amino-butyl-benzoate, or of p-(lower)alkylaminosalicylic acid 2-dimethylaminoethyl ester.

The Schiff Reaction product between homocysteine thiolactone and penaldates (N-acylamino malonaldehydic acids), using the ethyl-phenyl penaldate, has anti-inflammatory properties. The introduction of other substituents (—OH, —NO$_2$, —NH$_2$, —Br) on the phenyl nucleus of the latter preparation enhances anti-infective characteristics thereof.

The formation of Schiff Bases from N-substituted phenothiazines are obtained in two forms: by reaction with a carbaldehyde function introduced into the nucleus in the 2- or 4-position or with an aldehyde group introduced into a lower alkyl, or a lower alkylpiperazinyl chain attached to the 10-position; both of these substitutions lead to sedative drugs. Similarly, for other cyclic groups the aldehyde function needed for reaction with a (mono)amino(mono)oxotetrahydrothiophene, e.g. homocysteine thiolactone, is introduced into the nucleus or into a side chain.

The formation of an imine condensate with a phenothiazine, e.g. dibenzothiazine, lacking N substitution is effected at the 1- or 3-position from corresponding monocarboxaldehydes; alternatively, symmetrical double Schiff Bases are obtained at the 2- and 8-, or at the 3- and 7-positions from the respective dicarboxaldehydes. The thus-obtained condensates, e.g., with homocysteine thiolactone are antiparasitic drugs.

Sedative and hypnotic drugs result from the corresponding condensation of, e.g., homocysteine thiolactone with 5-(lower)alkyl-5-ethylaldehyde barbituric acid and analogous compounds.

Among the compounds derived from heterocyclic aldehydes, nitro derivatives, such as nitropiperonal, nitrothiophene, nitroquinoline, nitroindoline and nitroimidazole Schiff Bases of, e.g., homocysteine thiolactone are of particular interest as anti-protazoan agents. Likewise, nitroanthracene Schiff Bases of, e.g., homocysteine thiolactone are also anti-protazoan agents.

The invention is not limited to condensates with one tetrahydrothiophene. When the aldehyde has more than one aldehyde function which is subject to the Schiff Reaction, the condensate of each or of any number thereof (not precluded by steric hindrance) is within the scope of this invention. When a condensate is formed with more than one mole of tetrahydrothiophene per mole of aldehyde-containing compound, the tetrahydrothiophene may be the same or different members of the selected group.

An object of the invention is to provide a new class of physiologically-active and pharmacologically-acceptable compounds which are Schiff Bases of (mono)oxotetrahydrothiophene(mono)imines. A further object is to provide additional compounds having the physiological activity of their precursors (with a functional group subject to the Schiff Reaction with a primary amine or modifiable to have such a functional group), but with reduced toxicity. A still further object is to bring out particular biological activities of precursors by the location of the functional group in their molecular structure. Other objects are apparent from the following description.

The present invention is directed to physiologically-active and pharmacologically-acceptable Schiff Bases of the formula:

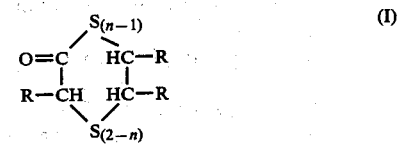

wherein
n is a positive whole number of at most 2;
one R is —N=R';
each other
R is —H; and
R' is the residue (=CH—R°) of an aldehyde from which the aldehyde oxygen atom has been removed.

When n=1, the compounds are of the formula:

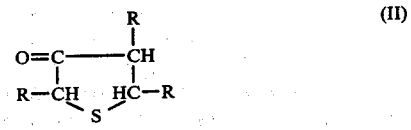

wherein R has its above-ascribed meaning.

They are Schiff Bases of 2-, 4- or 5-amino-3-oxo-tetrahydrothiophene. When n=2, the compounds are of the formula:

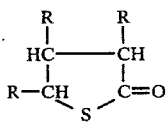

(III)

wherein R has its above-ascribed meaning. These compounds are Schiff Bases of 3-, 4- or 5-amino-2-oxo-tetrahydrothiophene.

Of the six noted subgenera of Schiff Bases those of 3-amino-2-oxotetrahydrothiophene are preferred for their outstanding activity and the availability of the starting material, homocysteine thiolactone (3-amino-2-oxotetrahydrothiophene.

The Schiff Bases are prepared (following generally-known procedures) in the same manner as disclosed by Dunn (U.S. Pat. No. 3,546,216) from monoamino-substituted tetrahydrothiophene-1,1-dioxides (differing from 2- or 3-oxotetrahydrothiophenes by the presence of $SO_2$ in the ring, which imparts a sulfone character, as indicated by their synonymic designation of "sulfolanes" or "tetramethylene sulfones"); there is only one amino group directly bound to the starting 2- or 3-oxotetrahydrothiophene, thus limiting the Schiff Bases to those of formula (I) wherein only one R is —N=R', and R' is not as limited as Dunn's $R^2CH=$. The sole limitation of R' is that the resulting Schiff Base be physiologically active and pharmacologically acceptable.

The Schiff Bases of this invention are prepared by contacting a monoamino-substituted 2- or 3-oxo-tetrahydrothiophene with an organic aldehyde having a carbaldehyde group, —CHO, directly bound to a carbon atom.

The organic aldehyde is virtually unlimited in its scope (except as previously indicated). Aliphatic, e.g. alkyl and substituted alkyl, aldehydes include such compounds as chloraldehyde (trichloroacetaldehyde monohydrate), butylchloralhydrate (2,2,3-trichlorobutane-1,1-diol) and valeraldehyde [yielding sedative-soporific agents] and undecylenic aldehyde (10-undecenal) [yielding an antifungal agent]; aromatic, e.g. substituted and unsubstituted 6-ring-membered monocarbocyclic to tricarbocyclic aromatic, aldehydes include such compounds as salicyaldehyde, anisaldehyde and their analogs [yielding an antimicrobial-antifungal agent], 4-benzamidosalicylaldehyde [yielding an antitubercular agent], p-aminoalkylbenzaldehyde, e.g. p-aminobutyl-benzaldehyde, and p-alkylaminosalicyl 2-dimethylaminoethylester, e.g. p-ethylaminosalicylaldehyde 2-di-methylaminoethylester [yielding local anesthetics] and 1-nitro-4-formylanthracene, nitroindoline and nitropiperonal [yielding anti-protozoan agents]; from 1- to 3-ring substituted or unsubstituted heterocyclic aromatic (having from 1 to 3, same or different, hetero atoms, such as a chalcogen, e.g. —O— or —S—, or nitrogen atom) aldehydes include such compounds as nitrothiophene, nitroquinoline and nitroimidazole [yielding anti-protozoan agents], N-ethyl-2- or 4-phenothiazinecarbaldehyde and N-(3-formylpropyl)phenothiazine [yielding sedatives], phenothiazine-1- or 3-monocarboxaldehyde [yielding anti-parasitic agents], 2,8-phenothiazinedicarbaldehyde and 3,7-phenothiazinedicarbaldehyde [yielding symmetrical double Schiff Bases which are anti-parasitic agents]; and nonaromatic heterocyclics include such compounds as 5-alkyl-5-(β-formylethyl)barbituric acid, e.g. 5-propyl-5-(β-formylethyl)barbituric acid [yielding a sedative and hypnotic agent].

There are only six contemplated starting tetrahydrothiophenes:

| | |
|---|---|
| 2-amino-3-oxo-tetrahydrothiophene | 3-amino-2-oxo-tetrahydrothiophene |
| 4-amino-3-oxo-tetrahydrothiophene | 4-amino-2-oxo-tetrahydrothiophene |
| 5-amino-3-oxo-tetrahydrothiophene | 5-amino-2-oxo-tetrahydrothiophene | and each is suitable for reaction with each and every carbaldehyde which undergoes the Schiff Reaction.

The six starting tetrahydrothiophenes are prepared from available starting materials according to analogy processes or from corresponding starting materials which are prepared from known compounds by established procedures. In this regard reference is made, e.g., to Canadian Pat. No. 611,437 for several syntheses of homocysteinethiolactone, i.e. 3-amino-2-oxo-tetrahydrothiophene. For embodiments wherein the oxo-group is in the 3-position, benzylamino-3-oxo-tetrahydrothiophene [prepared, e.g., as in the synthesis of biotin reported by Acheson, R. M., "The Chemistry of Heterocyclic Compounds", 2nd Edition, pp 138 to 140, Wiley International Edition, Interscience Publishers, New York-London, 1967] is subjected to alkaline hydrolysis to obtain the corresponding free amino compound. The 2-, 4- or 5-amino-3-oxo-tetrahydrothiophene is prepared by this procedure or by an analogy procedure from corresponding starting materials.

As is readily appreciated from the preceding indications, the primary pharmacological activity of the resulting Schiff Base is imparted thereto by the selected aldehyde rather than by the oxotetrahydrothiophene. The noted pharmacological activity applies to the resulting Schiff Base irrespective of the contemplated tetrahydrothiophene with which the noted aldehyde is condensed. The stated indications apply to those Schiff Bases prepared from each of the stated aldehydes and, e.g., from homocysteine thiolactone. Accordingly, examples with any of the encompassed tetrahydrothiophenes is equally illustrative for any of the other tetrahydrothiophenes. The pharmacologically-active and physiologically-acceptable oxotetrahydrothiopheneimines of this invention are useful in the same manner, for the same purposes, for the same recipients, at the same dosages and according to the same regimes as their active precursors (containing or modified to contain a formaldehyde or other function subject to the Schiff Reaction). Because of reduced toxicity, dosage and duration of treatment can be increased without further adverse affects. Administration of the pharmacologically-active and physiologically-acceptable imines is in the same mode and of the same dosage forms, e.g. tablets, capsules, solutions and ampoules, as those according to which the pharmacologically-active component thereof is administered. The dosage forms are prepared in the same way with the same inert components, including excipients, fillers, coloring, flavors and other additaments, while maintaining the same active-component concentration.

Referring to the Schiff Base condensates merely as imines, those obtained from benzaldehyde or from substituted benzaldehydes, e.g. salicyaldehyde, and from homocyclic or from heterocyclic arylpenaldates, e.g. phenylpenaldates, have anti-inflammatory properties. Imines of nitrofurans (prepared, e.g., by condensation with 5-nitrofuraldehyde) and of other nitro-substituted heterocyclics, e.g. nitropiperonal, nitrothiophenes, nitroquinolines, nitroindolines and nitroimidazoles, or of nitro-substituted carbocyclic aromatics, e.g. nitroanthracenes, are chemotherapeutic agents against the parasite of the Chagas disease.

EXAMPLE 1

N-(p-nitrobenzylidene)-2-oxotetrahydro-3-thiophenine

Mix an aqueous solution of homocysteine thiolactone hydrochloride (4.6 grams) with an ethanolic solution of p-nitrobenzaldehyde (4.6 grams). Stir the resulting reaction mixture and then add 2 percent (by weight) aqueous NaOH dropwise thereto until a pH of 6.0 is reached, at which time turbidity appears in the thus-prepared suspension. The turbidity is followed shortly thereafter by the formation of yellow crystals. Leave the suspension in a refrigerator (5° C.) until crystallization is complete before filtering out the yellow crystals. Recrystallize the filtered crystals of the title compound (m.p. 114° to 116° C.) from the aqueous ethanol.

EXAMPLE 2

N-[(2-ethoxycarbonyl-2-benzoylamino)ethylidene-(1)]-2-oxotetraydro-3-thiophenine Dissolve 30.6 grams of DL-homocysteine thiolactone hydrochloride in 280 ml of ethanol and 160 ml of water and add 51.6 grams of ethyl-phenyl sodium penaldate (dissolved in 150 ml of water) to the resulting solution. After a while a slight turbidity appears. Filter and then maintain for an extended period in a refrigerator to obtain a mass of white crystals. Wash and then recrystallize these crystals to obtain the title compound [m.p. 128° to 130° C.].

The elemental composition (percent by weight) calculated for $C_{16}H_{18}N_2O_4S$ is: C 57.5 H 5.4 N 8.2 O 19.2 S 9.5;
for 2 preparations prepared according to this example:
(a) C 57.3 H 5.43 N 8.08 O 19.31 S 9.61.
(b) C 57.43 H 5.48 N 8.39 S 9.52.

A biological study revealed that massive oral doses (up to 4 g/kg of body weight) administered repeatedly are tolerated without side effects.

Any penaldic acid is similarly condensed to form a corresponding Schiff Base. Replacing the ethyl-phenyl-penaldate, e.g., with an equivalent of ethyl-(o-hydroxyphenyl)penaldate or of ethyl-(o-acetylphenyl)penaldate results in a more analgesic-antipyretic anti-inflammatory drug of high tolerance.

Replacing the ethyl-phenyl-penaldate with an equivalent of ethyl-(o-nitrophenyl)-penaldate results in a drug with chemotherapeutic activity. The nature of benzene-ring substitution in the penaldic acid influences the pharmacological character of the condensate.

The title compound was investigated for anti-inflammatory activity, using D-dimethylcysteine as a control drug (penicillamine), a drug with well-established antirheumatic-antiarthritic action (references in: Crouzet, Guillen, Boullenger, Camus, Lièvre, *Revue du Rhumatisme*, 39, 601–607, 1972; and Keele & Lyle, *The Lancet*, 1, No. 7802, 549, 1973). Experimental data are summarized in Table I, showing that (in most cases) the title compound induced a greater effect on inflammatory response than the same dose of D-penicillamine (as indicated by the reduction of the oedema in comparison of the untreated control groups). In addition to the data presented in Table I (where egg-white was used as inflammatory agent) the following results were obtained in an experiment with an inflammation induced by dextran:

| | | Reduction in relation to controls |
|---|---|---|
| Phenylbutazone | 300 mg/kg per os | −8.4% |
| Title Compound | 200 mg/kg per os | −9.1% |
| Title Compound | 400 mg/kg per os | −7.6% |
| Title Compound | 800 mg/kg per os | −24.2% |
| Untreated controls | | −0 |
| | | (Inflamm. vol. +76.0%) |

Four rats (observed 5 times in the course of 2 hours, i.e. the values given for each group are based on 20 determinations) were included in each group of this experiment. The results indicate that the title compound is as effective as phenylbutazone in the dextran-induced inflammation, but it has a considerably higher therapeutic index since it is less toxic.

The inflammatory effect of Concanavaline A (W. T. Shier, *Proc. Soc. Exp. Biol. and Med.*, 146: 590–593, 1974) is reduced almost one third (31.8%) by two successive administrations of 500 mg/kg of the title compound.

TABLE I

THERAPEUTIC INFLUENCE OF THE ORAL TREATMENT WITH THE TITLE COMPOUND OF EXAMPLE 2 ON EGG-WHITE-INDUCED INFLAMMATION IN THE HIND LEGS OF ALBINO RATS (SPRAGUE-DAWLEY STRAIN)

| Experiment Number | Drug | Dose mg/kg | No. rats used | Observation** period (h) (No. observat.) | % Reduction of the inflammation compared to controls |
|---|---|---|---|---|---|
| 207 | D-Penicillamine | 300 | 4 | 3½ h (28) | −7.9 |
| | Title compound | 100 | 4 | 3½ h (28) | −15.4 |
| | Title compound | 200 | 4 | 3½ h (28) | −16.4 |
| | Title compound | 300 | 4 | 3½ h (28) | −21.4 |
| | Gum Arabic alone | 0 | 4 | 3½ h (28) | 0 (+96.1%)* |
| 211 | Homocysteine Thiolactone. HCl | 250 | 6 | 3 h (36) | −5.8 |
| | D-Penicillamine | 250 | 6 | 3 h (36) | −10.2 |
| | Title Compound | 250 | 6 | 3 h (36) | −10.9 |
| | Gum Arabic alone | 0 | 8 | 3 h (48) | 0 (+86.9%)* |
| 213 | D-Penicillamine | 1000 | 6 | 2 h (30) | −8.1 |
| | Title Compound | 1000 | 6 | 2 h (30) | −12.1 |
| | Gum Arabic alone | 0 | 8 | 2 h (30) | 0 (+88.4%)* |

TABLE I-continued
THERAPEUTIC INFLUENCE OF THE ORAL TREATMENT WITH THE TITLE COMPOUND OF EXAMPLE 2 ON EGG-WHITE-INDUCED INFLAMMATION IN THE HIND LEGS OF ALBINO RATS (SPRAGUE-DAWLEY STRAIN)

| Experiment Number | Drug | Dose mg/kg | No. rats used | Observation** period (h) (No. observat.) | % Reduction of the inflammation compared to controls |
|---|---|---|---|---|---|
| 215 | Title Compound | 300 | 5 | 2 h (25) | −18.0 |
| | Au-Penicillamine subcutaneous | 100 | 5 | 2 h (25) | −11.9 |
| | Gum Arabic alone | 0 | 5 | 2 h (25) | 0 (+81.5%)* |
| 219 | Title Compound | 200 | 4 | 2½ h (24) | −4.9 |
| | Title Compound | 400 | 4 | 2½ h (24) | −11.8 |
| | Title Compound | 800 | 4 | 2½ h (24) | −13.2 |
| | Gum Arabic alone | 0 | 6 | 2½ h (36) | 0 (+83.7%)* |
| 221 | Phenylbutazone | 500 (toxic) | 2 | 2 h (10) | −12.2 |
| | Title Compound | 500 | 3 | 2 h (15) | −11.0 |
| | None | 0 | 3 | 2 h (15) | 0 (+91.1%)* |
| 223/a | Title Compound | 1000 | 6 | 3 h (36) | −26.2 |
| | None | 0 | 16 | 3 h (96) | 0 (+70.9%)* |

*Increase of the volume determined plethysmographically over the pre-inflammation value. This is the inflammatory response of the untreated controls to which the effect of the drug treatment of the other groups is compared.
**Period of the observation after inflammatory challenge (h); in parentheses the total number of determinations made during this period on the whole group. The "Inflammatory Coefficient" is given by the average of this value and is deducted from that resulting for the untreated controls.

A single intraperitoneal dose of 250 mg/kg injected in a saline suspension to rats challenged with egg white (4 animals per group) reduced the Inflammatory Coefficient from 87.0 to 64.7%, i.e. it gave a 25.6% reduction.

Oral administration in the form of microcrystals further increases the effectiveness of the title compound absorption; this gives a steeper rise to the dose-effect curve (notice its flatness in the example presented on page 12—no difference between 200 and 400 mg/kg in the dextran experiment; the somewhat lower effect of the 400 mg/kg dose falls within the random fluctuation range in animal groups of equal response). The somewhat lower effect of the 400 mg/kg dose falls within the random fluctuation range in animal groups of equal response).

EXAMPLE 3

N-(o-hydroxybenzylidene)-2-oxotetrahydro-3-thiophenine

Mix a solution of 1.53 g of DL-homocysteine thiolactone in aqueous ethanol (10 to 14 ml) and an equimolar amount of salicylaldehyde (1.22 g) dissolved in 10 ml of ethanol. Add 0.1 N NaOH dropwise to the resulting reaction mixture. At pH 6 the formation of a light-yellow solid material becomes noticeable. Maintain at a low temperature, e.g. under refrigeration, until crystallization is complete. Thoroughly wash produced crystals and recrystallize to obtain the title compound as a yellow solid with a m.p. of 102° C. The calculated percentages for $C_{11}H_{11}NOS$ are:

C 59.73 H 4.98 N 6.33 O 14.48 S 14.48; those of the thus-obtained compounds are: C 59.70 H 4.88 N 6.14 O 14.70 S 14.34 N 6.16 O 14.59.

Another preparation made under similar conditions starting with 24.3 g of salicylaldehyde gave an 80% yield.

Repeated administration of doses as high as 2 g/kg (by the oral route) to mice and rats induces no toxic reactions or pathological changes.

The anti-inflammatory effect of the title compound was determined with accurate quantitative methods (*Proc. Soc. Ex. Biol. & Med.*, 136, 1328-1331, 1971).

Inflammation of the hind-legs induced by various mediators in the rat was plethysmographically measured at various time intervals on groups treated with this drug, on untreated controls and on animals treated with control drugs. Thus, the differences in the inflammatory response among groups ("Inflammatory Coefficient") are based on a number of determinations of significant value.

The numerical results are not identical in all experiments due to certain general variations in the conditions of the animals and their sensitivity to the inflammatory challenge; therefore, comparisons are based only on evaluations made in the same experiment using a group of animals for each drug. Besides, the effectiveness of a dosage has to be related to its tolerance.

It is significant of the high-inflammatory activity of the title compound that the minimal dose (by oral administration) which gave a detectable, though moderate, effect (5.5% reduction) was 50 mg/kg, i.e. less than 1/40th of the tolerated dose.

By the oral administration of a total of 400 mg/kg of suspension in 2% gum arabic (to stabilize the suspension), in two subdivided doses, 1.5 and 0.5 hour before inflammatory challenge with egg-white, the reduction of the inflammatory process was 17.06% with this new drug. Using an adentical amount of phenylbutazone (as control drug) in the same experiment, the reduction was 15.75%. At this dose level the two drugs gave an anti-inflammatory response of the tolerated dose for the new preparation, in the case of phenylbutazone it approaches the toxic level. The homocysteine thiolactone Schiff Base of salicylaldehyde in thus an effective anti-inflammatory drug in a fraction of its tolerated dose.

EXAMPLE 4

N-(5-methyl-3-phenyl-4-isoxazole)methylidene-2-oxotetrahydro-3-thiophenine

Following the procedure of Example 3 and replacing the salicylaldehyde with an equivalent of 4-formyl-5-methyl-3-phenylisoxazole results in the corresponding preparation of the title compound.

Replacing the salicylaldehyde of Example 3 with an equivalent of benzaldehyde, of 2-furaldehyde, or of p-aminobenzaldehyde results in the preparation of the corresponding imine of tetrahydrothiophenine.

EXAMPLE 5

N-(4-amino-2-methoxycarbonyl-3-oxo-4-phenyl)butylidene-2-oxotetrahydro-3-thiophenine Condense homocysteine thiolactone hydrochloride with an equimolar amount of 4-amino-2-methoxycarbonyl-3-oxo-4-phenylbutyraldehyde according to the procedure of Example 1 to obtain the title compound.

Replacing the butyraldehyde with an equivalent of:
4-amino-2-ethoxycarbonyl-3-oxo-4-phenylbutyraldehyde,
4-amino-4-furyl-2-methoxycarbonyl-3-oxobutyraldehyde,
4-amino-2-methoxycarbonyl-3-oxo-4-thienylbutyraldehyde,
4-amino-2-ethoxycarbonyl-3-oxo-4-pyrrolylbutyraldehyde,
4-amino-4-(2-imidazolyl)-2-methoxycarbonyl-3-oxobutyraldehyde,
4-amino-2-methoxycarbonyl-4-(2-oxazolyl)-3-oxobutyraldehyde,
4-amino-2-methoxycarbonyl-3-oxo-4-(2-thiazolyl)-butyraldehyde,
4-amino-2-methoxycarbonyl-3-oxo-4-(3-pyridyl)-butyraldehyde,
4-amino-2-methoxycarbonyl-3-oxo-4-(4-pyrimidinyl)-butyraldehyde, or
4-amino-4-(2-benzimidazolyl)-2-ethoxycarbonyl-3-oxobutyraldehyde
results in the preparation of the corresponding imine of tetrahydrothiophenine. The methoxycarbonyl or ethoxycarbonyl group at the 2-position is similarly replaced by any other lower alkoxy (or substituted lower alkoxy) group. Similarly, the ring component at the 4-position is virtually replaceable by any other component as long as the resulting Schiff Base is physiologically active and pharmacologically acceptable.

EXAMPLE 6

N-(5-nitro-2-furyl)methylidene-2-oxotetrahydro-3-thiophenine

Condense homocysteine thiolactone hydrochloride with an equimolar amount of 5-nitrofurfural according to the procedure of Example 1 to obtain the title compound.

Replacing the 5-nitrofurfural with an equivalent of:
5-nitropiperonal,
2-formyl-5-nitrothiophene,
2-nitro-5-quinolinecarbaldehyde,
3-nitro-4-indolinecarbaldehyde,
4-nitro-1-anthracenecarbaldehyde,
2-nitro-5-anthracenecarbaldehyde,
5-nitro-1-antracenecarbaldehyde, or
4-nitro-2-imidazolecarbaldehyde
yields corresponding nitro-substituted amines which are useful in therapy against hemoparasites.

EXAMPLE 7

3-carboxy-2-methoxytolyl-4,5-di-(N-methylidene-2-oxotetrahydro-3-thiophenine)

Condense two mole of homocysteine thiolactone hydrochloride with one moles of gladiolic acid according to the procedure of Example 1 to obtain the title compound, which is an antifungal antibiotic of low toxicity that is useful in the same manner and for the same purposes as gladiolic acid.

The corresponding monothiophenines are similarly prepared from equimolar amounts of the respective reactants and are used in the same manner and for the same purpose.

EXAMPLE 8

N-(2,2,3-trichloro)butylidene-2-oxotetrahydro-3-thiophenine

Condense homocysteine thiolactone hydrochloride with an equimolar amount of 2,2,3-trichlorobutyraldehyde according to the procedure of Example 1 to obtain the title compound.

Replacing the trichlorobutyraldehyde with an equivalent of chloral, of butylchloralhydrate or of p-chlorobenzaldehyde yields corresponding chloro-substituted imines of tetrahydrothiophenine.

EXAMPLE 9

N-(cyclopentyl)methylidene-3-oxotetrahydro-2-thiophenine

Condense equimolar amounts of 2-amino-3-oxotetrahydrothiophene and formylcyclopentane according to the procedure of Example 1 to obtain the title compound. Replacing the cyclopentane with an equivalent of 3-cyclohexenecarbaldehyde or of valeraldehyde results in the corresponding preparation of N-(3-cyclohexenyl)methylidene-3-oxotetrahydro-2-thiophenine or of N-(n-pentylidene)-3-oxotetrahydrothiophenine, respectively.

EXAMPLE 10

N-(1-naphthyl)methylidene-3-oxotetrahydro-2-thiophenine

Condense equimolar amounts of 2-amino-3-oxotetrahydrothiophene and 1-naphthalenecarbaldeyde according to the procedure of Example 1 to obtain the title compound. Replacing the carbaldehyde with an equivalent of 2-furaldehyde, of 3-thiophenecarbaldehyde or of 4-pyridinecarbaldehyde results in the corresponding preparation of N-(2-furyl)methylidene-3-oxotetrahydro-2-thiophenine, of N-(3-thienyl)methylidene-3-oxotetrahydro-2-thiophenine or of N-(4-pyridyl)methylidene-3-oxotetrahydro-2-thiophenine, respectively.

EXAMPLE 11

N-(2-quinolyl)methylidene-3-oxotetrahydro-4-thiophenine

Condense equimolar amounts of 4-amino-3-oxotetrahydrothiophene and 2-quinolinecarbaldehyde according to the procedure of Example 1 to obtain the title compound. Replacing the carbaldehyde with an equivalent of formylcyclohexane, of 2-naphthalenecarbaldehyde, or of 3-pyridinecarbaldehyde, results in the corresponding preparation of N-cyclohexylmethylidene-3-oxotetrahydro-4-thiophenine, of N-(2-naphthyl)methylidene-3-oxotetrahydro-4-thiophenine or of N-(3-pyridyl)methylidene-3-oxotetrahydro-4-thiophenine, respectively.

EXAMPLE 12

N-(3-pyrazolyl)methylidene-3-oxotetrahydro-4-thiophenine

Condense equimolar amounts of 4-amino-3-oxotetrahydrothiophene and 3-pyrazolecarbaldehyde according to the procedure of Example 1 to obtain the title compound. Replacing the carbaldehyde with an equivalent of 2-pyrimidinecarbaldehyde, of 3,5-dibromosalicylaldehyde or of 4-isoquinolinecarbaldehyde results in the corresponding preparation of N-(2-pyrimidinyl)methylidene-3-oxo-tetrahydro-4-thiophenine, of N-(3,5-dibromosalicyl)methylidene-3-oxotetrahydro-4-thiophenine or of N-(4-isoquinolyl)methylidene-3-oxotetrahydro-4-thiophenine, respectively.

EXAMPLE 13

N-[1,2(4H)-oxazin-4-yl]methylidene-3-oxotetrahydro-5-thiophenine

Condense equimolar amounts of 5-amino-3-oxotetrahydrothiophene and 4-[1,2(4H)-oxazine]carbaldehyde according to the procedure of Example 1 to obtain the title compound. Replacing the carbaldehyde with an equivalent of 3-furancarbaldehyde, of 5-quinolinecarbaldehyde or of 6-indolecarbaldehyde results in the corresponding preparation of N-(3-furyl)methylidene-3-oxotetrahydro-5-thiophenine, of N-(5-quinolyl)methylidene-3-oxotetrahydro-5-thiophenine or of N-(6-indolyl)methylidene-3-oxotetrahydro-5-thiophenine, respectively.

EXAMPLE 14

N-(4-benzofuranyl)methylidene-3-oxotetrahydro-5-thiophenine

Condense equimolar amounts of 5-amino-3-oxotetrahydrothiophene and 4-benzofurancarbaldehyde according to the procedure of Example 1 to obtain the title compound. Replacing the carbaldehyde with an equivalent of 1-isoquinolinecarbaldehyde, of 5-pyrimidinecarbaldehyde or of 2-[1,2(2H)-thiazine]carbaldehye results in the corresponding preparation of N-(1-isoquinolylmethylidene-3-oxotetrahydro-5-thiophenine, of N-(5-pyrimidinyl)methylidene-3-oxotetrahydro-5-thiophenine or of N-[1,2(2H)-thiazin-2-yl]methylidene-3-oxotetrahydro-5-thiophenine, respectively.

EXAMPLE 15

N-(9-acridinyl)methylidene-2-oxotetrahydro-3-thiophenine

Repeating Example 1 and replacing the p-nitrobenzaldehyde therein with an equivalent of 9-acridinecarbaldehyde results in the corresponding preparation of the title compound. Replacing the p-nitrobenzaldehyde with an equivalent of 6-purancarbaldehyde, of 2-(1,3,5-triazine)carbaldehyde or of 7-pteridinecarbaldehyde instead results in the coresponding preparation of N-(6-puranyl)methylidene-2-oxotetrahydro-3-thiophenine, of N-(1,3,5-triazin-2-yl)methylidene-2-oxotetrahydro-3-thiophenine or of N-(7-pteridinyl)methylidene-2-oxotetrahydro-3-thiophenine, respectively.

EXAMPLE 16

N-(1-tricyclo[3,3,1,1$^{3,7}$]decyl)methylidene-2-oxotetrahydro-4-thiophenine Condense equimolar amounts of 4-amino-2-oxotetrahydrothiophene and 1-tricyclo[3,3,1,1$^{3,7}$]decanecarbaldehyde according to the procedure of Example 1 to obtain the title compound. Replacing the carbaldehyde with an equivalent of 2-thiophenecarbaldehyde, of 7-quinolinecarbaldehyde or of 5-[1,2(6H)-oxazine]carbaldehyde results in the correspondng preparation of N-(2-thienyl)methylidene-2-oxotetrahydro-4-thiophenine, of N-(7-quinolyl)methylidene-2-oxotetrahydro-4-thiophenine or of N-[1,2(6H)-oxazin-2-yl]methylidene-2-oxotetrahydro-4-thiophenine, respectively.

EXAMPLE 17

N-(2-pyridyl)methylidene-2-oxotetrahydro-4-thiophenine

Condense equimolar amounts of 4-amino-2-oxotetrahydrothiophene and 2-pyridinecarbaldehyde according to the procedure of Example 1 to obtain the title compound. Replacing the carbaldehyde with an equivalent of 3(2H)-pyrancarbaldehyde, of 8-isoquinolinecarbaldehyde or of 2-[1,3-(4H)-oxazine]carbaldehyde results in the corresponding preparation of N(2H)-pyran-3-ylmethylidene-2-oxotetrahydro-4-thiophenine, of N-(8-isoquinolyl)methylidine-2-oxotetrahydro-4-thiophenine or of N-[1,3(4H)-oxazin-2-yl]methylidene-2-oxotetrahydro-4-thiophenine, respectively.

EXAMPLE 18

N-(1-indolizinyl)methylidene-2-oxotetrahydro-5-thiophenine

Condense equimolar amounts of 5-amino-2-oxotetrahydrothiophene and 1-indolizinecarbaldehyde according to the procedure of Example 1 to obtain the title compound. Replacing the carbaldehyde with an equivalent of 3-isobenzofurancarbaldehyde, of 2-dibenzofurancarbaldehyde or of 8-(2H)-chromencarbaldehyde results in the corresponding preparation of N-(3-isobenzofuranyl)methylidene-2-oxotetrahydro-5-thiophenine, of N-(2-dibenzofuranyl)methylidene-2-oxotetrahydro-5-thiophenine or of N-(2H)-chromen-8-ylmethylidene-2-oxotetrahydro-5-thiophenine, respectively.

EXAMPLE 19

N-(2-benzo[b]thienyl)methylidene-2-oxotetrahydro-5-thiophenine

Condense equimolar amounts of 5-amino-5-oxotetrahydro-5-thiophene and 2-benzo[b]thiophenecarbaldehyde according to the procedure of Example 1 to obtain the title compound. Replacing the carbaldehyde with an equivalent of 1-phenanthridinecarbaldehyde, of 2-(4H)-pyrancarbaldehyde or of 4-pyrazolecarbaldehyde results in the corresponding preparation of N-(1-phenanthridinyl)-methylidene-2-oxotetrahydro-5-thiophenine, of N-(4H)-pyran-2-ylmethylidene-2-oxotetrahydro-5-thiophenine or of N-(4-pyrazolyl)methylidene-2-oxotetrahydro-5-thiophenine, respectively.

EXAMPLE 20

Following the procedure of Example 1, condense homocysteine thiolactone hydrochloride with an equimolar amount of each of the following:

2,2-di(carbamoyloxymethyl)pentanecarbaldehyde {meprobamate},
2-sulfanilamido-1,3,4-thiadiazole-5-carbaldehyde {sulfamethizole},
5-formylmethyl-5-phenylbarbituric acid {phenobarbital},
2,4-diamino-5-(p-chlorophenyl)-6-(β-formyl)ethylpyrimidine {pyrimethamine},
6-purinethiol-8-carbaldehyde {mercaptopurine},
8-(1-hydrazino)phthalazinecarbaldehyde {hydralazine},
2-[3-o-tolyl-4(3H)-equinazolinone]carbaldehyde {methaqualone},
4-(6,7-dimethoxy-1-veratryl)isoquinolinecarbaldehyde {papaverine},
4-(3-formyl)propyl-1,2-diphenyl-3,5-pyrazolidinedione {phenylbutazone},
5-(3-dimethylaminopropyl)-10,11-dihydro-5H-dibenz[b,f]azepine-2-carbaldehyde {imipramine},
10,11-dihydro-10-formyl-N-methyl-5H-dibenzo[a,d]cycloheptene-Δ$^{5,\gamma}$-propylamine {nortriptyline},
10,11-dihydro-N,N-dimethyl-2-formyl-5H-dibenzo[a,d]cycloheptene-Δ$^{5,\gamma}$-propylamine {amitriptylene},
1-(p-chlorobenzoyl)-7-formyl-5-methoxy-2-methylindole-3-acetic acid {indomethacin},
D(-)-threo-2-dichloroacetamido-1-(2-formyl-4-nitro)-phenyl-1,3-propanediol {chloramphenicol},
5-(p-formyl)phenyl-5-phenyl-2,4-imidazolidinedione {diphenylhydantoin},
1-(p-chloro-α-phenylbenzyl)-4-(m-formylbenzyl)piperazine {meclizine},
7-chloro-2-methylamino-5-(p-formyl)phenyl-3H-1,4-benzodiazepine-4-oxide {chlordiazepoxide},
7-chloro-1,3-dihydro-5-(p-formyl)phenyl-1-methyl-2H-1,4-benzodiazepin-2-one {diazepam},
10-[2-(4-formyl-1-methyl-2-piperidyl)ethyl]-2-(methylthio)phenothiazine {thioridazine},
5-(2-[p-chloro-α-(2-dimethylaminoethyl)benzyl]-pyridine)carbaldehyde {chlorpheniramime},
2-phenothiazinecarbaldehyde {phenothiazine},
4-phenothiazinecarbaldehyde {phenothiazine},
10-(3-formylpropyl)phenothiazine, and
10-[4-(β-formylethyl)piperazin-1-yl]phenothiazine
to obtain the corresponding 2-oxotetrahydro-3-thiophenine.

The designated recognized medicament set forth in { } is that upon which the immediately-preceding reactant (aldehyde) is based. The resulting Schiff Base condensate is useful in the same doses (giving the equivalent blood-organ levels) in the same dosage forms, for the same conditions, according to the same mode of administration, at the same frequency and duration of administration with substantially the same therapeutic results (but with less toxicity) as obtained by the similar administration of the designated recognized medicament. As the Schiff Base condensates are solids, the dosage forms are prepared in the same manner as those for the corresponding recognized medicament whenever such recognized medicament is also a solid; the concentration of the Schiff Base in the dosage forms is the same as that of such medicament in corresponding dosage forms, and the excipients, carriers, fillers, coloring matter, flavor and other additaments are likewise present in substantially the same proportions.

EXAMPLE 21

Replacing the homocysteine thiolactone hydrochloride with an equimolar amount of each of the following:

2-amino-3-oxotetrahydrothiophene,
4-amino-3-oxotetrahydrothiophene,
5-amino-3-oxotetrahydrothiophene,
4-amino-2-oxotetrahydrothiophene, and
5-amino-2-oxotetrahydrothiophene,
repeat Example 20 to obtain the corresponding oxotetrahydrothiophenines.

EXAMPLE 22

Repeating Example 1 and replacing the p-nitrobenzaldehyde therein with an equivalent of 2-thiazolidinecarbaldehyde, of p-formylphenylacetic acid, of (1-naphthyl)acetaldehyde, of acrylaldehyde, of cinnamaldehyde or of nicotinaldehyde results in the preparation of the corresponding 2-oxotetrahydro-3-thiophenine.

EXAMPLE 23

Repeating Example 1 and replacing the p-nitrobenzaldehyde therein with two equivalents of 1,2-naphthalenedicarbaldehyde, of (1-naphthylmethyl)-malonaldehyde, of 3-[4-(formylmethyl)-1-naphthyl]propionaldehyde, of p-anisaldehyde or of terephthalaldehyde results in the preparation of the respective corresponding di-(2-oxotetrahydro-3-thiophenine).

The invention and its advantages are readily understood from the preceding description. Various changes may be made in the structures of compounds, in the position of the oxotetrahydrothiophene moiety and in the conditions employed for the condensation reaction without departing from the spirit or scope of the invention or sacrificing its material advantages. The hereinbefore-described and exemplified process and compounds are merely illustrative, the selected compounds being somewhat indicative of the scope of structures that are amenable to the disclosed treatment.

What is claimed is:

1. Pharmacologically-active and physiologically-acceptable butyrothiolactonimine which is a Schiff Base of an aminobutyrothiolactone and a penaldate; the butyrothiolactone ring of which is further unsubstituted and the imine nitrogen of which is directly bound to two carbon atoms, one of which is a ring carbon of said butyrothiolactone ring.

2. A 3-oxotetrahydro-2-thiophenine according to claim 1.

3. A 3-oxotetrahydro-4-thiophenine according to claim 1.

4. A 3-oxotetrahydro-5-thiophenine according to claim 1.

5. A 2-oxotetrahydro-3-thiophenine according to claim 1.

6. A 2-oxotetrahydro-4-thiophenine according to claim 1.

7. A 2-oxotetrahydro-5-thiophenine according to claim 1.

8. The imine according to claim 1 which is N-[(2-ethoxycarbonyl-2-benzoylamino)ethylidene-(1)]-2-oxotetrahydro-3-thiophenine.

9. The imine which is N-(o-hydroxybenzylidene)-2-oxotetrahydro-3-thiophenine.

10. The imine which is N-(5-methyl-3-phenyl-4-isoxazole)methylidene-2-oxotetrahydro-3-thiophenine.

11. The imine which is N-(4-amino-2-methoxycarbonyl-3-oxo-4-phenyl)butylidene-2-oxotetrahydro-3-thiophenine.

12. The imine which is N-(5-nitro-2-furyl)methylidene-2-oxotetrahydro-3-thiophenine.

13. The imine which is N-(2,2,3-trichloro)butylidene-2-oxotetrahydro-3-thiophenine.

14. A pharmaceutically-acceptable anti-inflammatory composition having an effective concentration of the imine according to claim 8.

15. An anti-inflammatory medicament composition having an effective concentration of the imine according to claim 9.

16. A process of reducing inflammation which comprises administering an effective amount of a medicament according to claim 15 to a subject afflicted with an inflammation.

17. A process of reducing inflammation which comprises administering an effective amount of a medicament according to claim 14 to a subject afflicted with an inflammation.

18. An anti-inflammatory Schiff Base according to claim 1.

19. A Schiff Base according to claim 18 wherein the penaldate is an ethyl-phenylpenaldate.

20. A pharmacologically-active and physiologically-acceptable butyrothiolactoneimine according to claim 1 which is a butyrothiolactone/o-hydroxybenzaldehyde condensate.

21. A butyrothiolactoneimine Schiff Base according to claim 1 which is an anisaldehyde/oxotetrahydrothiophenine condensate.

22. A Schiff Base according to claim 1 which is a Schiff Base of an arylpenaldate and an oxotetrahydrothiophenine.

23. A Schiff Base according to claim 22 wherein the arylpenaldate is ethyl-(o-hydroxyphenyl)penaldate.

24. A Schiff Base according to claim 22 wherein the arylpenaldate is ethyl-(o-acetylphenyl)penaldate.

25. A pharmacologically-active and physiologically-acceptable butyrothiolactoneimine, which is an aminobutyrothiolactone/(benzaldehyde or substituted benzaldehyde) Schiff Base having a butyrothiolactone ring that is further unsubstituted and in the structure of which the imine nitrogen is directly bound to two carbon atoms, one of which is a ring carbon atom of the butyrothiolactone ring.

* * * * *

UNITED STATES PATENT AND TRADEMARK OFFICE
CERTIFICATE OF CORRECTION

PATENT NO. : 4,344,956

DATED : August 17, 1982

INVENTOR(S) : Nicolo ERCOLI

It is certified that error appears in the above-identified patent and that said Letters Patent are hereby corrected as shown below:

Title page, at [56] References Cited, insert under "U.S. PATENT DOCUMENTS", --3,068,100 12/1962 Dersch 96/66; 3,372,193 3/68 Moffett 260/566; 3,584,049 6/71 Schmitt 260/566F--. Start a new heading --FOREIGN PATENT DOCUMENTS-- and list underneath --611,437 12/1960 Canada--. Start a new heading --OTHER PUBLICATIONS-- and list underneath --Ackeson, R.M., "The Chemistry of Heterocyclic Compounds", 2nd Edition, pages 138 to 140, Wiley International Edition, Interscience Publishers, New York-London, 1967; Bock et al., Arzneim.-Forsch. (Drug. Res.), 22, No. 9a, pages 1564 and 1565, 1972; Newton, B.A., "Chemotherapy of Trypanosomiasis and Leishmaniasis", page 287, Ciba Foundation Symposium 20, Elsevier, Amsterdam, 1974; The Van Nostrand Chemist's Dictionary (1961), page 626--. Column 2, line 28, "naphtyl" should read --naphthyl--. Column 4, lines 15 and 17, "protazoan" should read --protozoan--. Column 5, line 47, "salicyaldehyde" should read --salicylaldehyde--. Column 9, lines 33 and 34, "on page 12" should read --in column 8, lines 25 to 35--. Column 11, line 58, "antracenecarbaldehyde" should read --anthracenecarbaldehyde--. Column 17, line 22, "claim 1" should read --claim 25--. Column 18, line 4, "claim 1" should read --claim 25--.

Signed and Sealed this

Twenty-first Day of August 1984

[SEAL]

Attest:

GERALD J. MOSSINGHOFF

Attesting Officer

Commissioner of Patents and Trademarks